United States Patent [19]
Gisselberg et al.

[11] Patent Number: 5,885,217
[45] Date of Patent: Mar. 23, 1999

[54] CATHETER INTRODUCER

[75] Inventors: Margo L. Gisselberg, Lynnwood; Allen J. Hicks, Woodinville, both of Wash.

[73] Assignee: Tyco Group S.A.R.L., Luxembourg

[21] Appl. No.: 375,768

[22] Filed: Jan. 20, 1995

[51] Int. Cl.$^6$ .................................................. A61B 5/00
[52] U.S. Cl. ........................ 600/434; 600/435; 604/164; 604/165
[58] Field of Search ................................ 604/160, 161, 604/164, 165, 282, 280; 600/434

[56] References Cited

U.S. PATENT DOCUMENTS

| | | | |
|---|---|---|---|
| 2,623,520 | 12/1952 | Bamford, Jr. et al. | 128/221 |
| 3,406,685 | 10/1968 | May | 128/214.4 |
| 4,013,080 | 3/1977 | Froning | 128/347 |
| 4,192,305 | 3/1980 | Seberg | 128/214.4 |
| 4,233,974 | 11/1980 | Desecki et al. | 128/215 |
| 4,345,606 | 8/1982 | Littleford | 128/784 |
| 4,362,156 | 12/1982 | Feller, Jr. et al. | 604/165 |
| 4,417,886 | 11/1983 | Frankhouser et al. | 604/53 |
| 4,431,426 | 2/1984 | Groshong et al. | 604/280 |
| 4,445,893 | 5/1984 | Bodicky | 604/165 |
| 4,549,879 | 10/1985 | Groshong et al. | 604/247 |
| 4,559,046 | 12/1985 | Groshong et al. | 604/282 |
| 4,609,370 | 9/1986 | Morrison | 604/165 |
| 4,675,007 | 6/1987 | Terry | 604/283 |
| 4,737,152 | 4/1988 | Alchas | 604/256 |
| 4,772,266 | 9/1988 | Groshong | 604/160 |
| 4,813,938 | 3/1989 | Raulerson | 604/167 |
| 4,955,890 | 9/1990 | Yamamoto et al. | 606/108 |
| 4,973,313 | 11/1990 | Katsaros et al. | 604/165 |
| 5,004,456 | 4/1991 | Botterbusch et al. | 604/53 |
| 5,064,414 | 11/1991 | Revane | 604/165 |
| 5,098,392 | 3/1992 | Fleischhacker et al. | 604/165 |
| 5,129,891 | 7/1992 | Young | 604/283 |
| 5,300,106 | 4/1994 | Dahl et al. | 607/119 |
| 5,312,337 | 5/1994 | Flaherty et al. | 604/93 |
| 5,352,205 | 10/1994 | Dales et al. | 604/158 |
| 5,409,469 | 4/1995 | Schaerf | 604/160 |

FOREIGN PATENT DOCUMENTS

| | | |
|---|---|---|
| 0008451 | 3/1980 | European Pat. Off. . |
| 0171077 | 2/1986 | European Pat. Off. . |
| 0258566 | 3/1988 | European Pat. Off. . |

*Primary Examiner*—Mark Hindenburg
*Assistant Examiner*—Pamela Wingood
*Attorney, Agent, or Firm*—Richard D. Allison; Monty Smith

[57] ABSTRACT

A catheter introducer which allows a dilator member and a sheath member to be engaged with and disengaged from each other promptly and smoothly. The catheter introducer includes a sheath member consisting of a sheath portion and a sheath hub and a dilator member consisting of a dilator portion and a dilator hub and a locking mechanism operatively connecting the sheath member and dilator member during the insertion of the catheter introducer into the body of the patient. The dilator hub includes one or more flange members associated therewith and the flange member is rotatable with respect to the sheath hub to selectively engage the sheath hub in a first position and disengage the sheath hub in a second position.

18 Claims, 14 Drawing Sheets

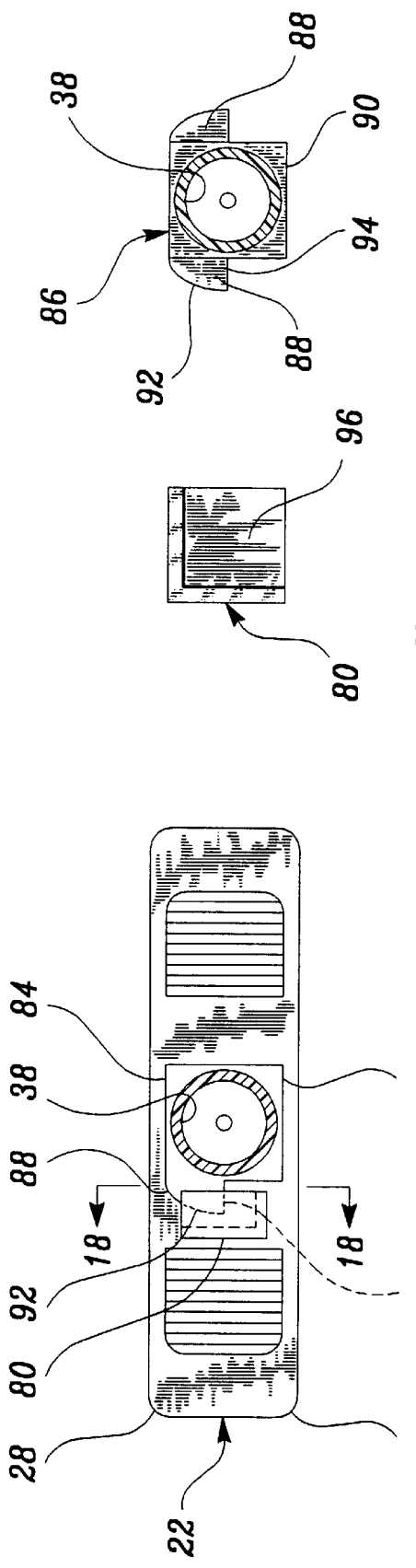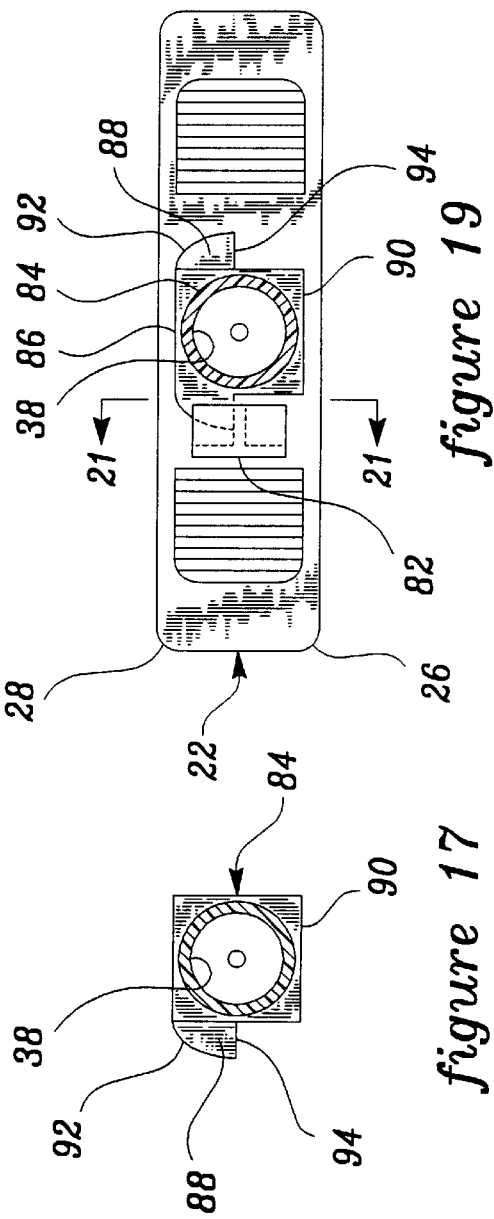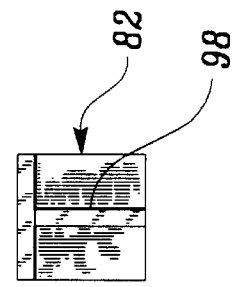

CATHETER INTRODUCER

TECHNICAL FIELD

The present device relates to an improved catheter introducer for introducing a catheter into a blood vessel.

BACKGROUND ART

A preferred non-surgical method for inserting a catheter involves the use of the Seldinger technique which includes an access needle that is inserted into the patient's vein. A guidewire is then inserted through the needle and into the vein. The needle is then removed and a dilator and sheath combination are then inserted over the guidewire. The dilator and sheath combination are then inserted a short distance into the tissue to dilate the incision and the dilator is then removed and discarded. The catheter is then inserted through the sheath into the vein in the desired location.

In a device to introduce a catheter into a blood vessel such as for angiography, hemodialysis or other vascular access procedures, a catheter introducer is used. As shown in FIG. 1, symbol 1 denotes a catheter introducer in general. The catheter introducer 1 includes a sheath member 2, a dilator member 3, a sheath hub 4, a sheath portion 5, a female hole 6, a dilator hub 7, a dilator portion 8, a male prism 9, and an optional side tube 10.

As can be seen in the drawing, the prior art catheter introducer 1 of FIG. 1 is composed of the sheath member 2 consisting of the sheath portion 5 and the sheath hub 4 and the dilator member 3 which consists of the dilator portion 8 and the dilator hub 7. The catheter introducer 1 has the dilator member 3 positioned in the sheath member 2, and is inserted into a blood vessel over a guide wire in the manner briefly described above.

FIGS. 2 and 3 are illustrations showing how the prior art catheter introducer of FIG. 1 may be used. In the drawings, symbol 11 denotes an optional three-way stop cock, a guide wire is designated by symbol 12, subcutaneous tissue is designated by symbol 13, and symbol 14 designates a blood vessel. When the catheter introducer 1 is used, a hollow needle (not illustrated) with an inner needle inserted through it is introduced into the blood vessel 14, and after removing the inner needle, the guide wire 12 is inserted through the hollow needle. The hollow needle is subsequently removed, to leave only the guide wire 12 in the blood vessel. Then, as shown in FIG. 2, the catheter introducer 1 with the dilator member 3 inserted in the sheath member 2 is inserted into the blood vessel 14 with the guide wire 12 operating as a guide. The catheter introducer 1 is introduced until the sheath portion 5 of the sheath member 2 is at least partially inserted into the blood vessel 14. As shown in FIG. 3, the dilator member 3 and the guide wire 12 may be subsequently removed. Then, a catheter is inserted into the sheath member 2 which operates to guide the tip of the catheter through the incision and into the blood vessel 14 to complete the insertion of the catheter. Subsequently, as desired, the three-way stop cock 11 may be actuated to supply a medicine, etc. into the blood vessel through the sheath member 2 or the sheath portion 5 of the sheath member 2 may be split or torn into two sections as the sheath member 2 is removed from around the catheter as described below.

During insertion of the catheter introducer 1 into the blood vessel 14, the sheath member 2 is typically held near the surface of the skin of the patient and gently twisted as the catheter introducer 1 is inserted through the subcutaneous tissue and into the vein of the patient. However, to achieve this, a mechanism for mutually arresting the movement of the dilator member 3 and the sheath member 2 is desired to prevent the relative rotation between the dilator member 3 and the sheath member 2 as well as to prevent the longitudinal displacement of the dilator member 3 relative to the sheath member 2.

To prevent the relative rotation and longitudinal displacement of the dilator member 3 with respect to the sheath member 2, several prior art devices have been disclosed. For example, the device as shown in FIG. 1 is disclosed in PCT Application No. US93/00437 and includes a female polygonal hole 6 formed in the sheath member 2 and a male prism 9 formed in the dilator member 3. The male prism 9 of the dilator member 3 is inserted in the female hole 6 of the sheath member 2 to prevent the relative rotation between the dilator member 3 and the sheath member 2. Furthermore, the female polygonal hole 6 has a groove 6a formed and the male prism 9 has a rib 9a formed so that when the male prism 9 of the dilator member 3 is inserted in the female polygonal hole 6 of the sheath member, the rib 9a of the male prism 9 is fitted in the groove 6a of the female polygonal hole 6 to resist the axial displacement of the dilator member 3 and the sheath member 2.

FIG. 4 shows a further prior art device disclosed in the PCT patent application. The male engaging part 15 of the dilator member 3 and the female engaging part 16 of the sheath member 2 are tapered and hexagonal in cross section. The tapered engagement between the dilator member 3 and the sheath member 2 can prevent the axial displacement and the relative rotation between the sheath member 2 and the dilator member 3.

The prior art device shown in FIGS. 5 and 6 is also disclosed in the PCT patent application. FIG. 5 is a front view showing the end of the sheath member 2 with a female taper portion 17 with recesses 18 and FIG. 6 is a side view showing the dilator member 3 with a male taper portion 19 with protrusions 20. The male taper portion 19 of the dilator member is inserted into the female taper portion 17 of the sheath member to prevent the axial displacement by the taper portion 17, and to prevent the relative rotation by the engagement between the protrusions 20 and the recesses 18.

The prior art device shown in FIG. 7 is also shown in the PCT patent application. In this device, a spiral protrusion 21 is formed around the end 2a of the sheath member and a recess 22 to be engaged with the protrusion 21 of the sheath member is formed on the end 3a of the dilator hub 7 for fastening the dilator member 3 and the sheath member 2 together.

Finally, an example of a further prior art catheter introducer device is shown in FIG. 8. This prior art device is assigned to the Assignee of the present invention and is more fully shown in Design U.S. Pat. No. 318,733. This type of catheter introducer device includes a pull apart sheath and may be used with oval or round catheters and dilators.

SUMMARY OF THE INVENTION

As described above, several mechanisms for engaging the dilator member with the sheath member have been disclosed. In many of the above described devices, the engagement is achieved by the interconnection of tapered members. This type of engagement is weak and unstable and may disengage during use.

The use of protrusions and recesses in the prior art device shown in FIGS. 5 and 6 overcomes this disadvantage to some extent. However, for reliable engagement between protrusions and recesses, the engagement between the elements must be secure enough to prevent disengagement therebetween. Additionally, it is desirable that the locking mechanism be readily observable by the user to enable the user to immediately determine if the locking mechanism is engaged or disengaged. Furthermore, it is desirable to provide the user with a tactile indication that the locking mechanism is engaged or disengaged.

The present invention has been created to solve the problems of the conventional catheter introducers described above, and an object of the present invention is to provide a catheter introducer which allows the dilator member to be engaged with and disengaged from the sheath member promptly and smoothly.

To achieve the above object, the catheter introducer of the present device has one or more enlarged flanges formed at the proximal end of the dilator hub. The flanges are aligned with a locking mechanism on the dilator hub to indicate when the proximal end of the sheath hub is in locking engagement with the dilator member. The flanges and locking mechanism on the dilator hub may be fixedly or rotatably secured to the dilator hub such that the flanges and locking member may be rotated relative to the dilator member if desired.

In one form of the catheter introducer of the present invention, the dilator hub of the dilator member may include a portion of the locking mechanism thereon such that when the dilator member is inserted into and rotated relative to the sheath member, a protrusion, tab or extension formed on the sheath hub of the sheath member or dilator hub of the dilator member is engaged with a groove or recessed area formed on the other of the dilator hub of the dilator member or the sheath hub of the sheath member to integrate the dilator member and the sheath member. With the locking mechanism of the present invention, even if the catheter introducer is inserted into the blood vessel while only the sheath member is being held and the sheath member is twisted during insertion, the dilator member and the sheath member rotate together and are not relatively or longitudinally displaced from each other.

In a preferred form of the present invention, the dilator member may be readily separated from the sheath member by slightly rotating flange members on the dilator hub with respect to the sheath hub to release the locking mechanism. The dilator member may then be withdrawn from the sheath member. The use of the flanges provides the user with a visual indication of when the locking mechanism is engaged because the flanges of the dilator hub are aligned with the handles of the sheath member to indicate when the locking mechanism is engaged and are misaligned with the handles of the sheath hub when the locking mechanism is disengaged. Additionally, the presence of tactile indicators on the dilator hub provide an indication to the user that the dilator member and sheath member are engaged with each other and also provide tactile indication if the locking mechanism between dilator hub and sheath hub should somehow become disengaged during insertion of the catheter introducer into the patient.

BRIEF DESCRIPTION OF DRAWINGS

FIG. 16 is a cross-sectional view similar to the views shown in FIGS. 11 and 14 showing the top portion of an alternate embodiment of the ledge area engaging the sheath member of the catheter introducer of the present invention;

FIG. 17 is a partial top view showing the modified extension area on the dilator member;

FIG. 18 is a partial side view taken generally along lines 18—18 of FIG. 16 showing the modified locking tab of the present embodiment;

FIG. 19 is a cross-sectional view similar to the views shown in FIGS. 11, 14 and 16 showing the top portion of an alternate embodiment of the ledge area engaging the sheath member of the catheter introducer of the present invention;

FIG. 20 is a partial top view showing the modified ledge area and extension areas on the dilator member;

FIG. 21 is a partial side view taken generally along lines 21—21 of FIG. 19 showing the modified locking tab of the present embodiment;

DESCRIPTION OF THE PREFERRED EMBODIMENTS

Figure 1:
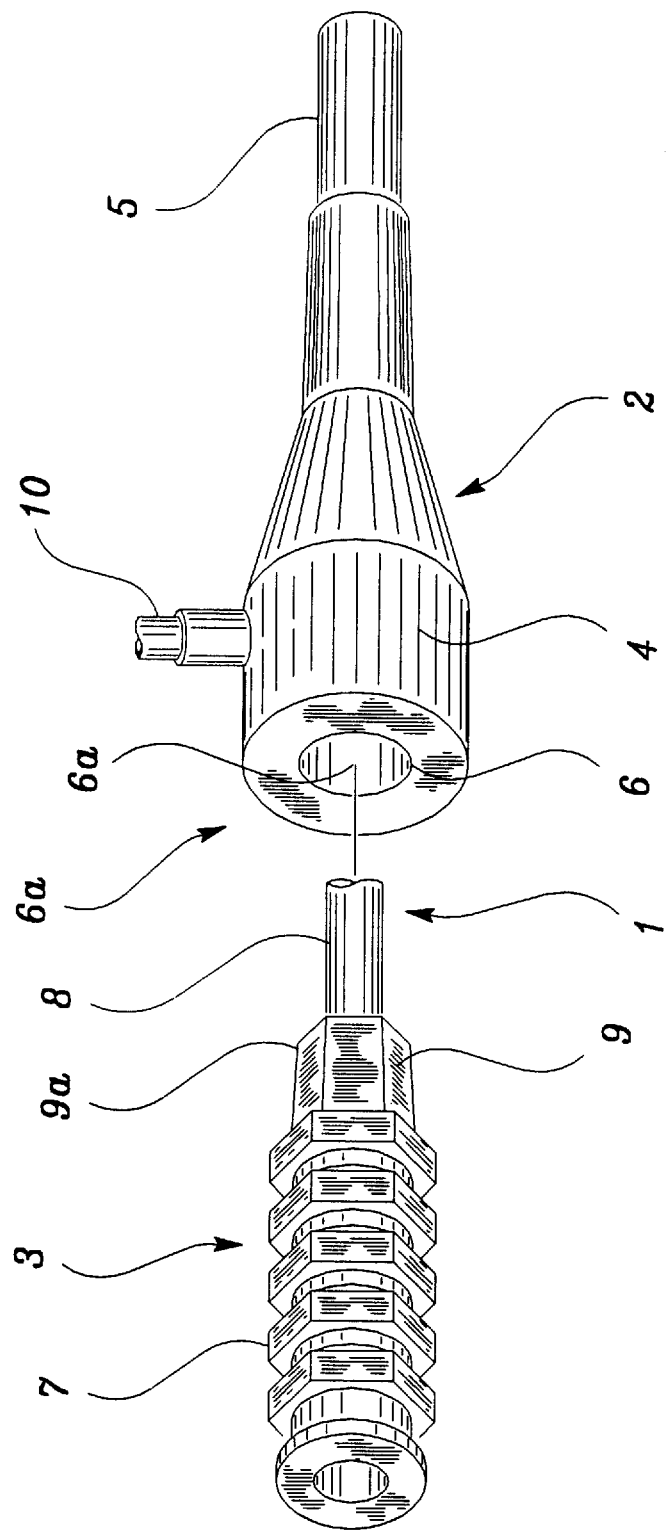
FIG. 1 is a side view showing a prior art catheter introducer.

FIGS. 1–8 are illustrative of various prior art catheter introducers, referred to herein generally as catheter introducer 1. The prior art catheter introducers consist generally of an elongate and generally tubular sheath member 2 and elongate dilator member 3 which is sized to be inserted into the sheath member 2. The sheath member 2 generally includes a sheath hub 4 on the proximal portion thereof and an elongate and tubular sheath portion 5 extending distally therefrom. The distal side of the sheath hub 4 generally includes a female hole 6 therein which is sized to receive the dilator portion 8 of the dilator member 3 therein. The proximal side of the dilator hub 7 includes a male prism 9 or similarly configured area thereon which is formed to lockingly engage the female hole 6 of the sheath hub 4. As can be seen in the drawings, the prior art catheter introducer 1 may also include a side tube 10 with a three way stop cock 11 thereon.

Figure 11:
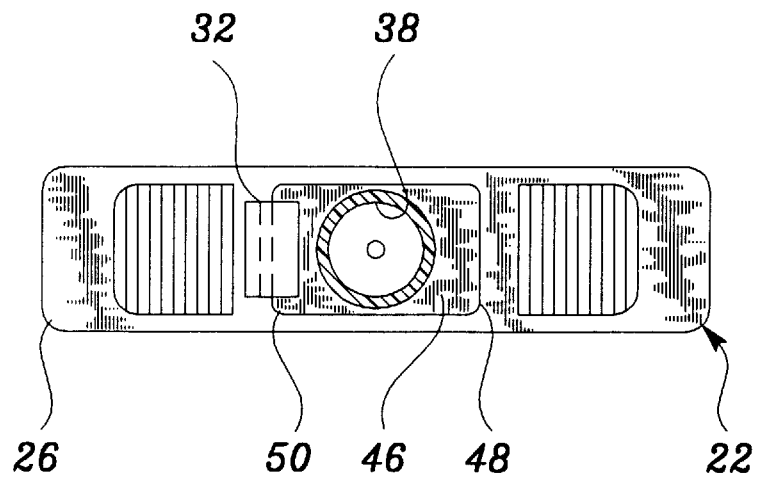
FIG. 11 is a cross-sectional view taken generally along lines 11—11 of FIG. 9 showing the engagement between the sheath member and ledge area of FIG. 9.

The catheter introducer 20 of the present invention generally includes a sheath member 22 and a dilator member 24. As shown in FIGS. 9–12, the sheath member 22 is preferably an oval-shaped tear apart sheath which includes a pair of handle members 26 extending laterally from the sheath hub 28. The sheath hub 28 preferably includes one or more slits 30 therein to facilitate the removal of the sheath member 22 from around a catheter as described more fully below. The proximal and distal sides of the handle members 26 may include ribs or other surfaces thereon to facilitate the grasping of the sheath member 22 by the user. As best shown in FIG. 11, the distal side of the sheath hub 28 preferably includes a generally L-shaped locking tab 32 extending therefrom. In this embodiment, the locking tab 32 extends upwardly from the top surface of one of the handle members 26 to engage a portion of the dilator member 24 as described below. The sheath portion 34 of the sheath member 22 is an elongate and flexible member which preferably has an oval-shaped cross section in the present embodiment. The sheath portion 34 extends distally from the sheath hub 28 and is inserted into the incision in the body of the patient generally in the manner shown in FIGS. 2 and 3.

Figure 12:
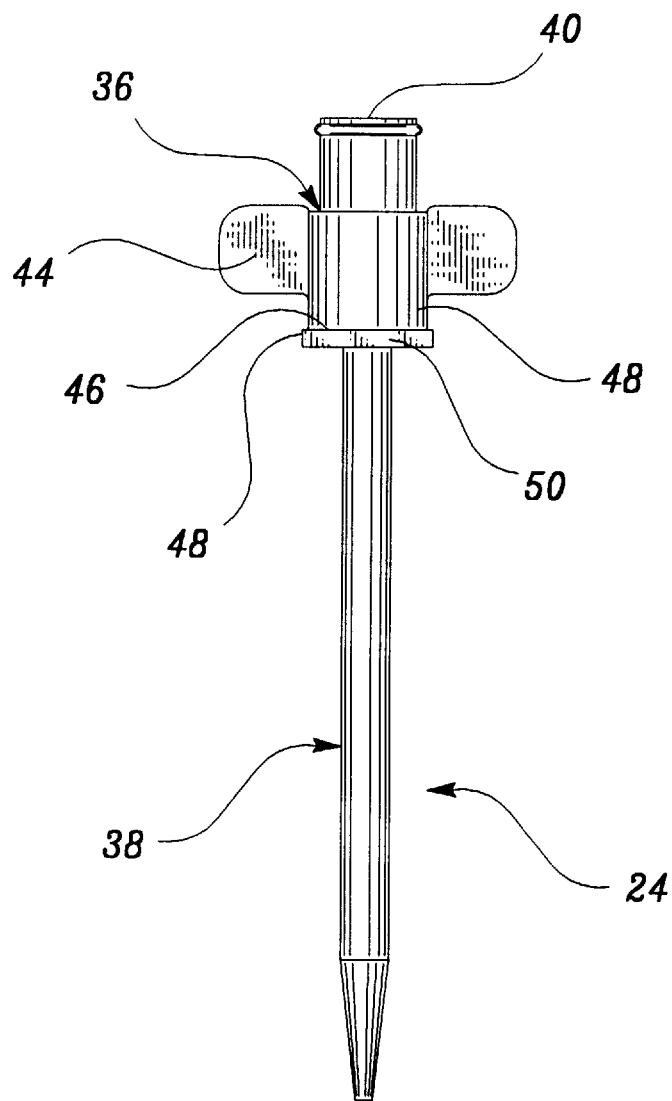
FIG. 12 is an enlarged perspective view showing the dilator member of FIG. 9.

The dilator member 24 of the embodiment shown in FIGS. 9–12 generally includes a dilator hub 36 and a dilator portion 38. The dilator hub 36 forms the distal end of the dilator member and includes a standard connector 40, such as a luer type of connector on the distal end thereof. The dilator member 24 is preferably a semi-rigid member having a lumen extending therethrough to receive a guide wire (not shown) therethrough. The dilator locking mechanism 42 is preferably positioned proximally of the standard connector 40 on or adjacent to the dilator hub 36. In this embodiment, the dilator locking mechanism 42 is rotatable with respect to the dilator member 24. The dilator locking mechanism 42 preferably includes a pair of enlarged and generally ear-shaped flange members 44 which extend laterally from the dilator hub 36 to provide a convenient surface for the user to grasp and manipulate during use. The dilator locking mechanism 42 of this embodiment also includes a laterally extending ledge area 46 on the distal portion thereof. The ledge area 46 consists of a pair of oppositely positioned extension areas 48 and a pair of oppositely positioned flat areas 50. In this embodiment, the extension areas 48 are lateral extensions which are aligned with the flange members 44 while the flat areas 50 are oriented generally perpendicular to the flange members 44 as shown in FIG. 12. The internal surface of the dilator locking mechanism 42 preferably includes a rib or similar member thereon which is received in a complementary member on the dilator hub 36 to allow the rotational movement of the dilator locking mechanism 42 with respect to the dilator hub 36 while preventing the longitudinal displacement thereof. The rotational movement of the dilator locking mechanism 42 is particularly desirable with the present embodiment due to the oval cross-sectional shape of the sheath portion 34 and dilator portion 38 of the present embodiment.

Figure 2:
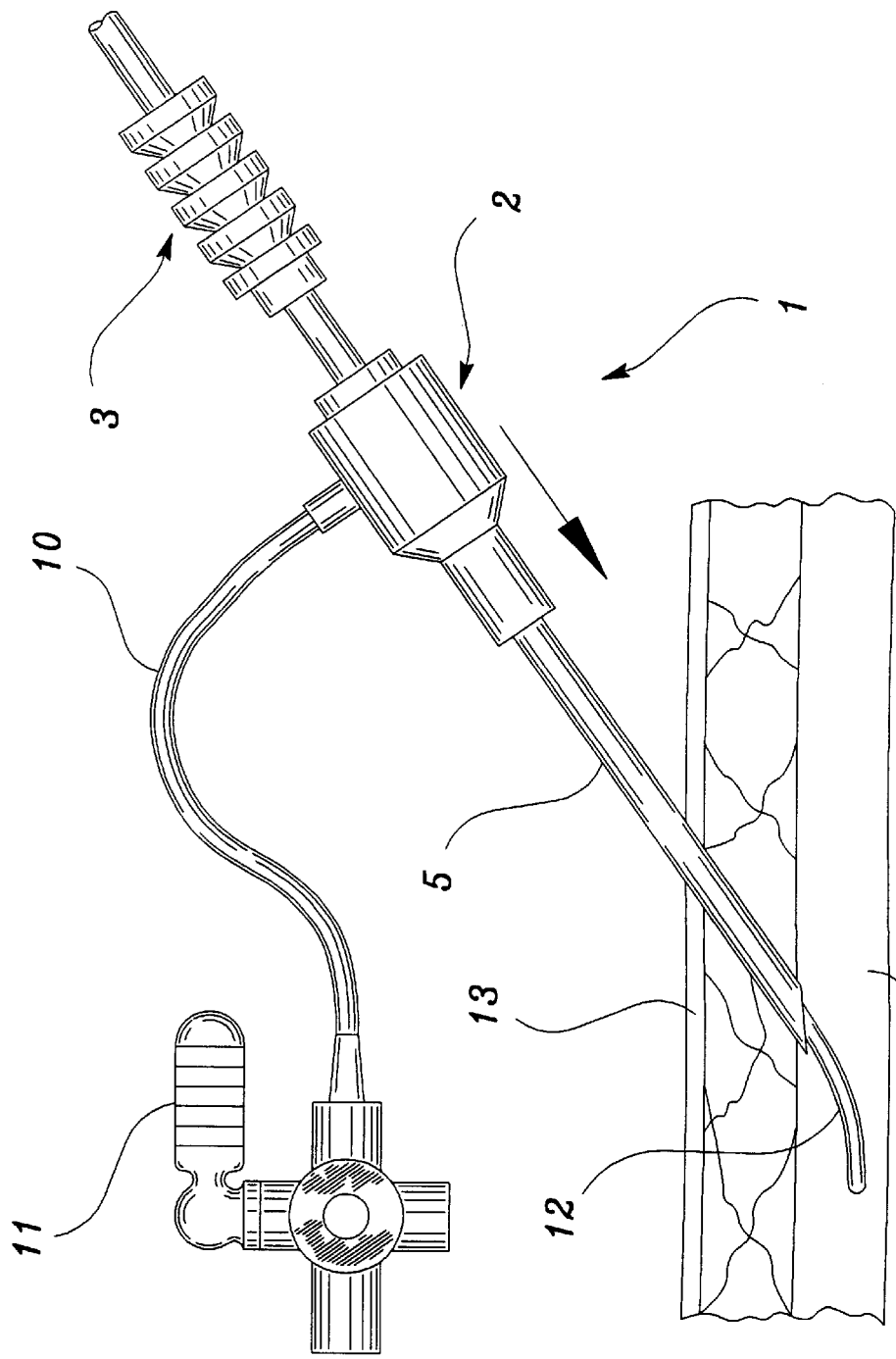
FIG. 2 is a side view of the prior art catheter introducer shown in FIG. 1, showing how the catheter introducer is used.
Figure 3:
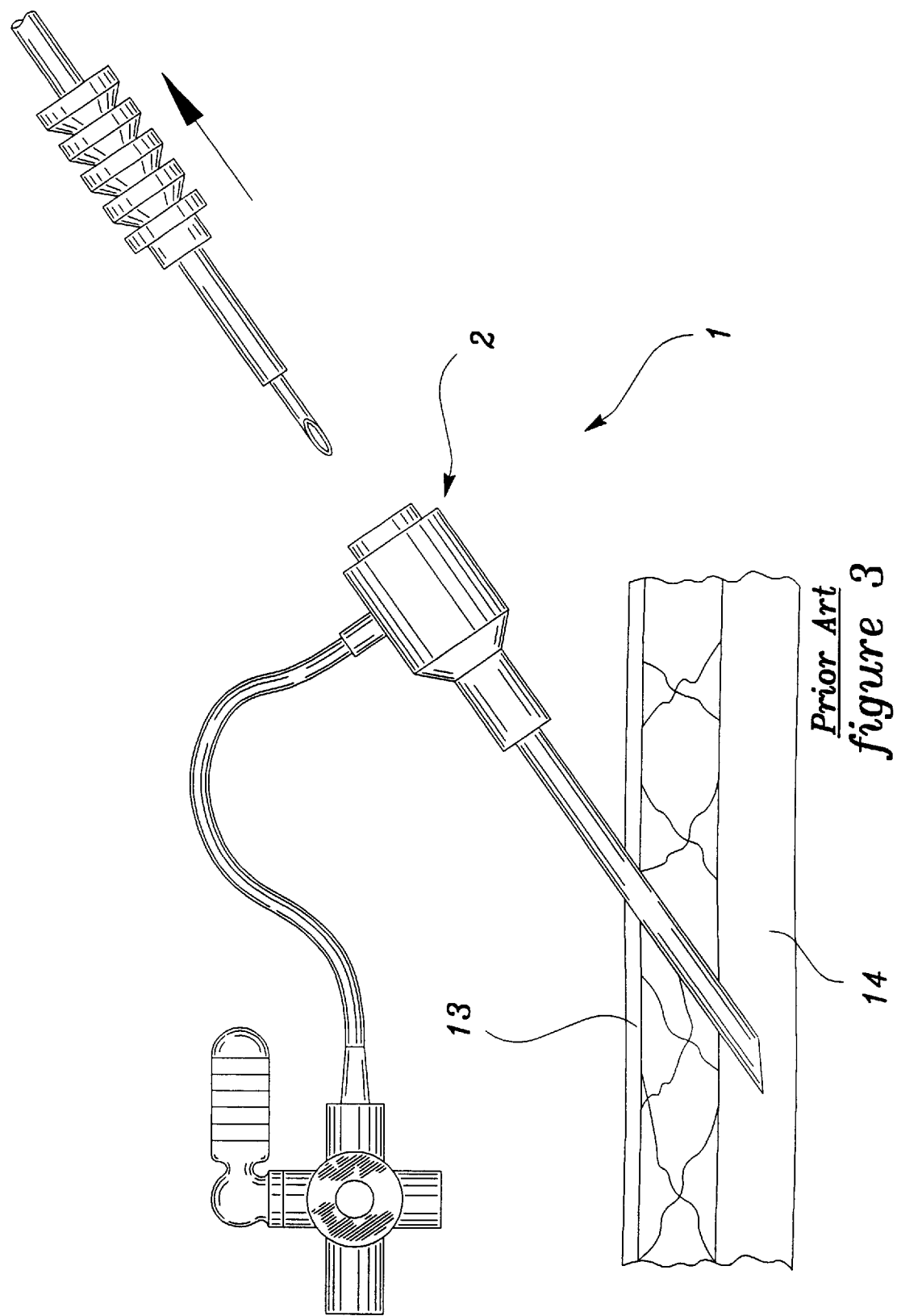
FIG. 3 is a side view of the catheter introducer further showing how the prior art catheter introducer is used.
Figure 4:
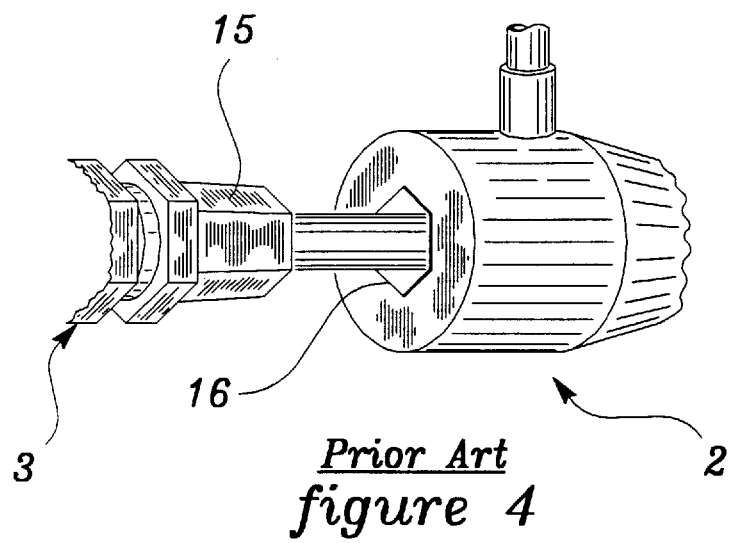
FIG. 4 is a partial perspective view showing a portion of a dilator inserted into a sheath hub of a prior art catheter introducer.
Figure 5:
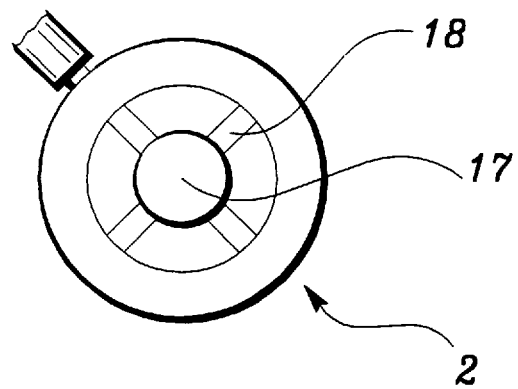
FIG. 5 is a partial front view showing the sheath hub of another prior art catheter introducer.
Figure 6:
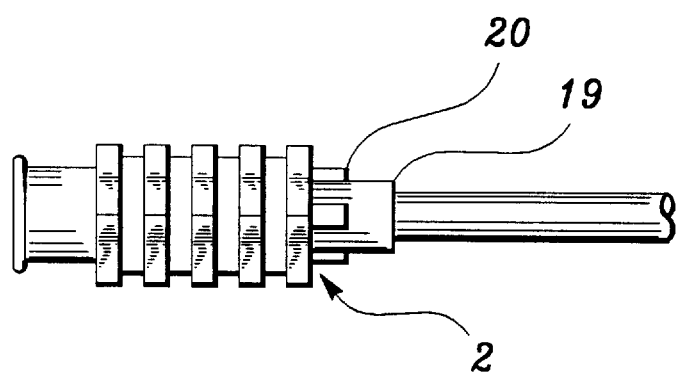
FIG. 6 is a partial side view showing the dilator section of the prior art catheter introducer shown in FIG. 5.
Figure 7:
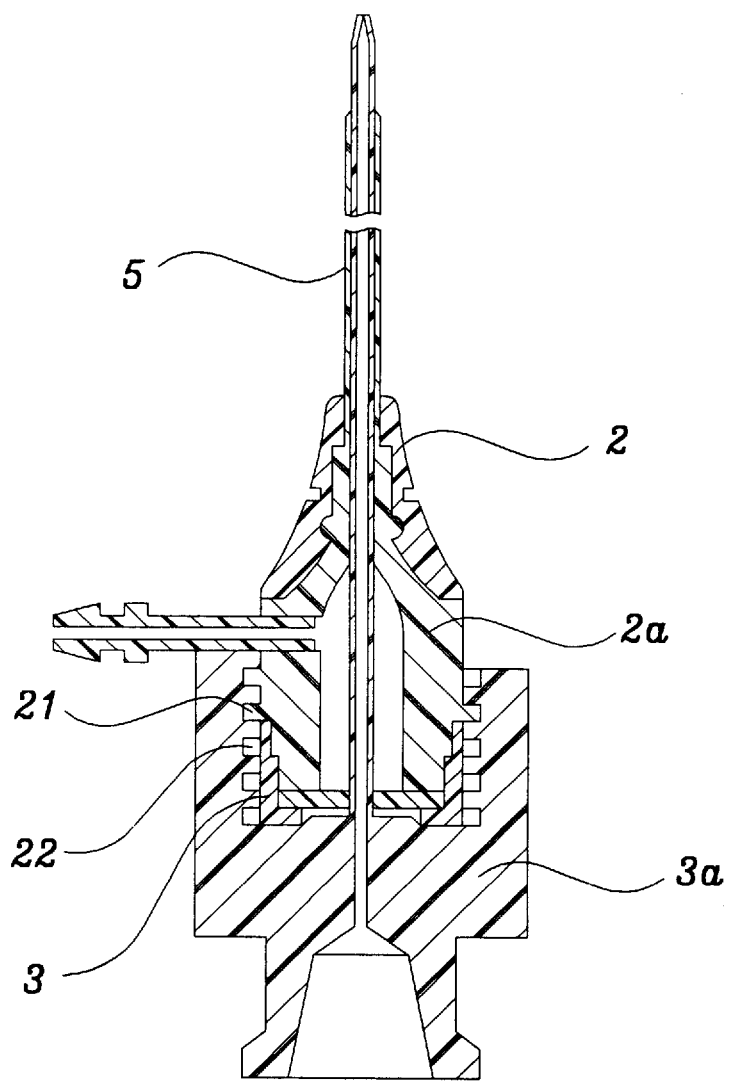
FIG. 7 is a cross-sectional view showing the threaded engagement between the dilator section and a sheath section of a prior art catheter introducer.
Figure 8:
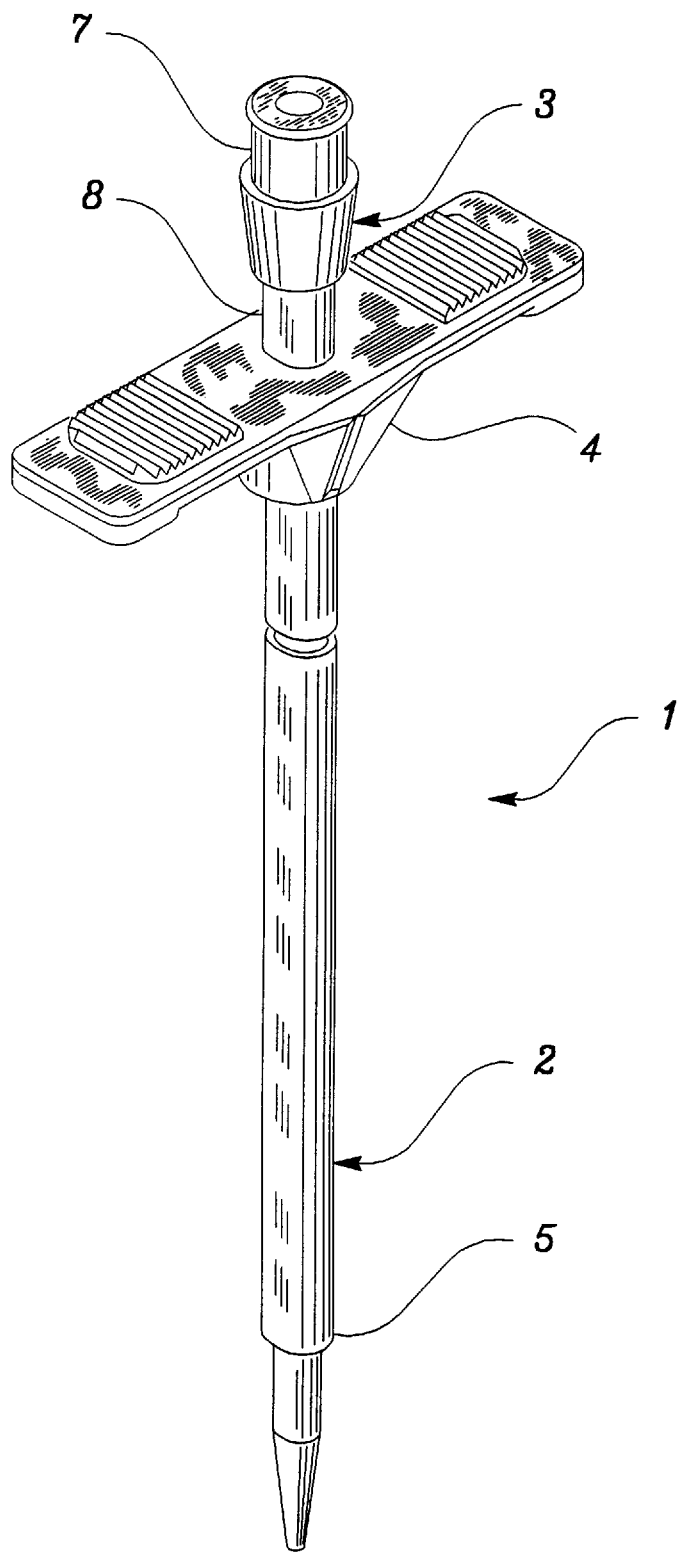
FIG. 8 is an elevated view showing a further prior art catheter introducer.
Figure 9:
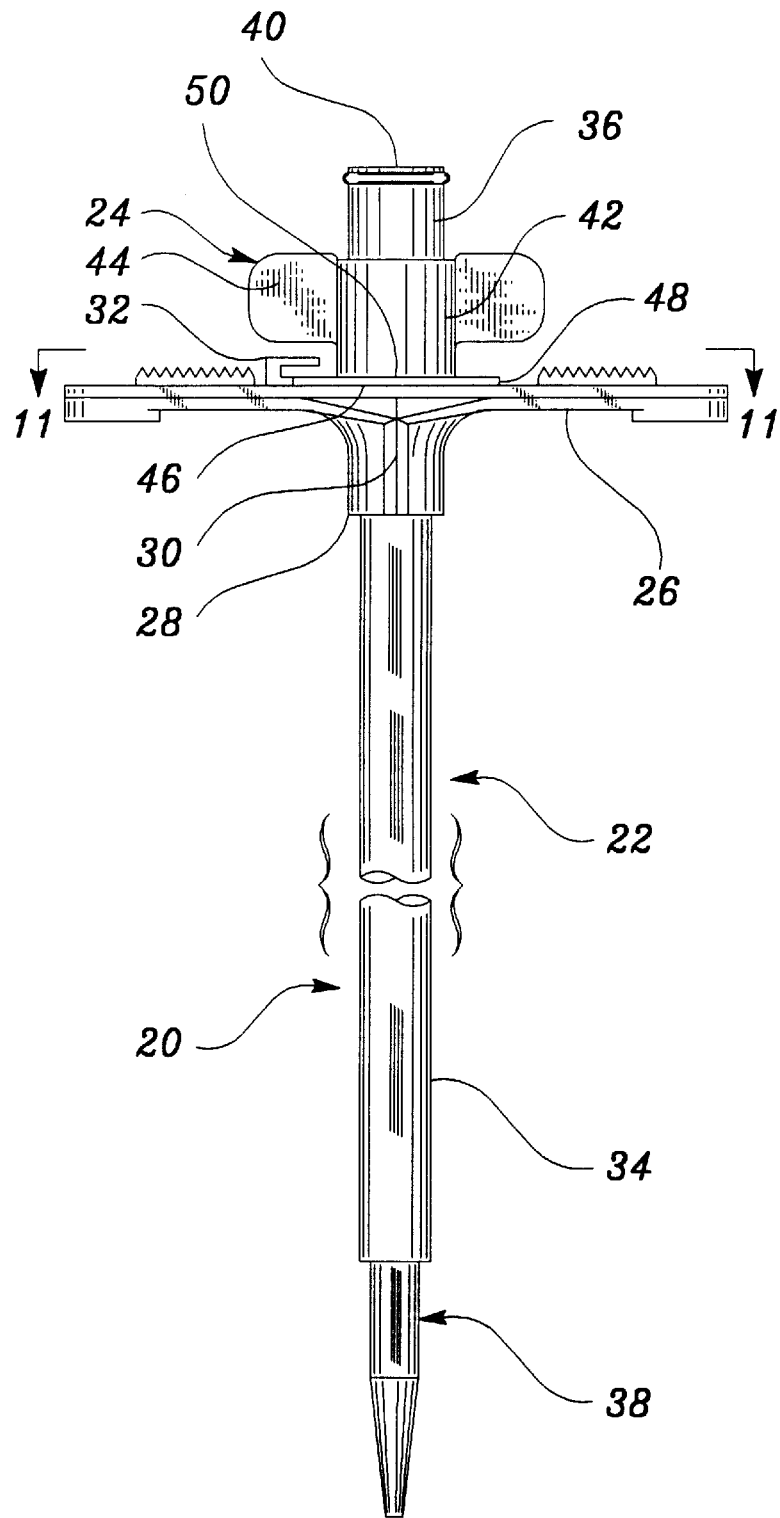
FIG. 9 is an enlarged perspective side view showing a catheter introducer as an example of the present invention with the locking mechanism between the dilator member and sheath member engaged.
Figure 10:
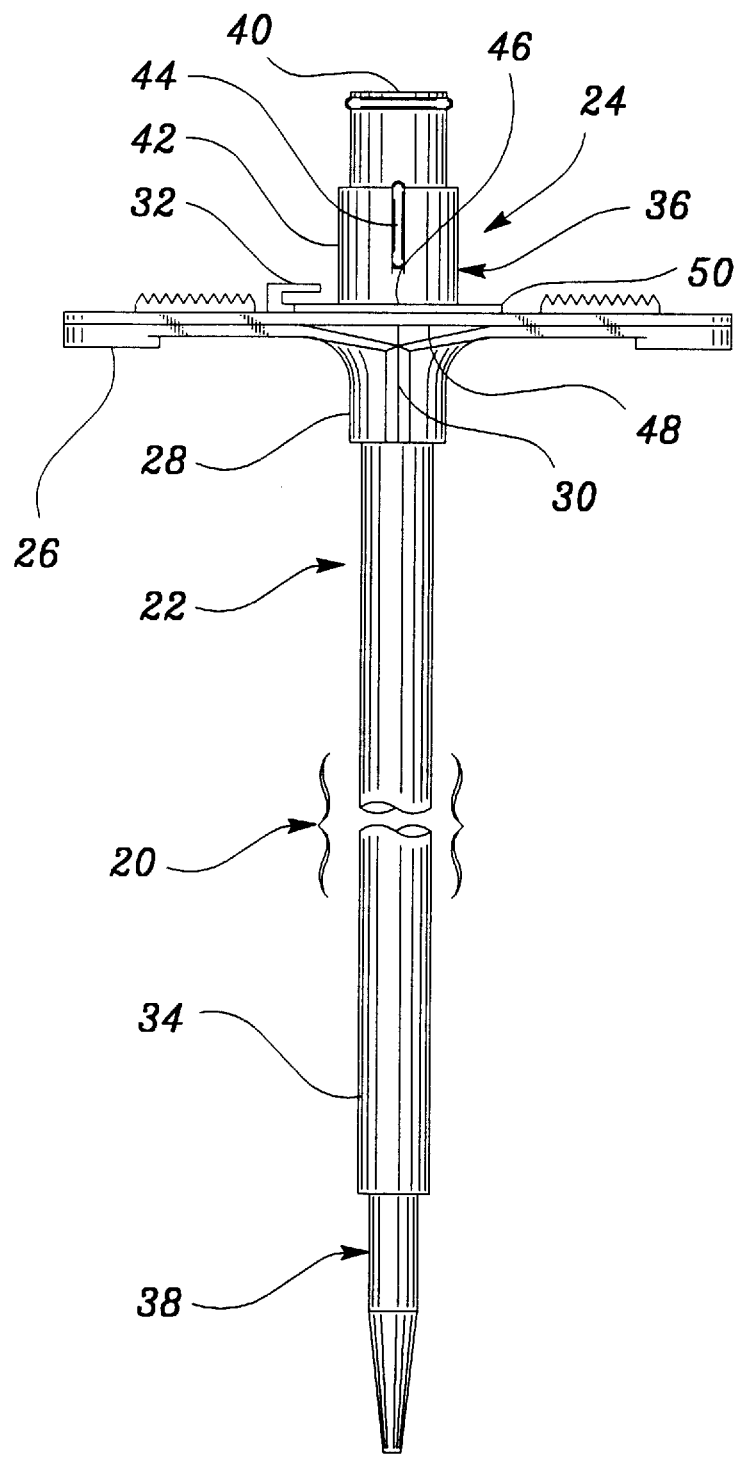
FIG. 10 is an enlarged perspective view showing the catheter introducer of FIG. 9 with the locking mechanism disengaged.

As generally illustrated in FIGS. 2 and 3 for the prior art catheter introducers, the catheter introducer 20 of the present invention includes the dilator portion 38 of the dilator member 24 which is sized to be snugly received in the interior of the sheath portion 34 of the sheath member 22. The dilator portion 38 is inserted into the sheath portion 34 until the dilator hub 36 is positioned adjacent to the proximal side of the sheath hub 28. As the dilator member 24 is inserted into the sheath member 22, the flange members 44 of the dilator locking mechanism 42 are preferably oriented generally perpendicularly to the handle members 26 on the sheath hub 28 so that one of the flat areas on the ledge area 46 is positioned adjacent to the locking tab 32 on the sheath hub 28. Once the dilator portion 38 is fully inserted into the sheath portion 34, the dilator locking mechanism 42 may be rotated with respect to the dilator hub 36 to position one of the extension areas 48 of the ledge area 46 between the locking tab 32 and distal surface of the sheath hub 28-to prevent further longitudinal movement between the dilator member 24 and the sheath member 22.

Once the catheter introducer 20 has been inserted into the patient and the incision is properly dilated, the dilator locking mechanism 42 may be rotated to an orientation wherein the flange members 44 are generally perpendicular to the handle members 26 to disengage the extension area 48 on the ledge area 46 of the dilator member 24 from the locking tab 32 of the sheath member 22. The user may then remove the dilator member 24 from the sheath member 22 and insert a catheter (not shown) through the sheath member 22. As is conventional with tear apart sheaths, the handle members 26 may be depressed with respect to the sheath hub 28 to tear the sheath hub 28 along the slits 30 and then the sheath portion 34 may then be torn after or as the catheter is inserted into the incision in the patient.

Figure 13:
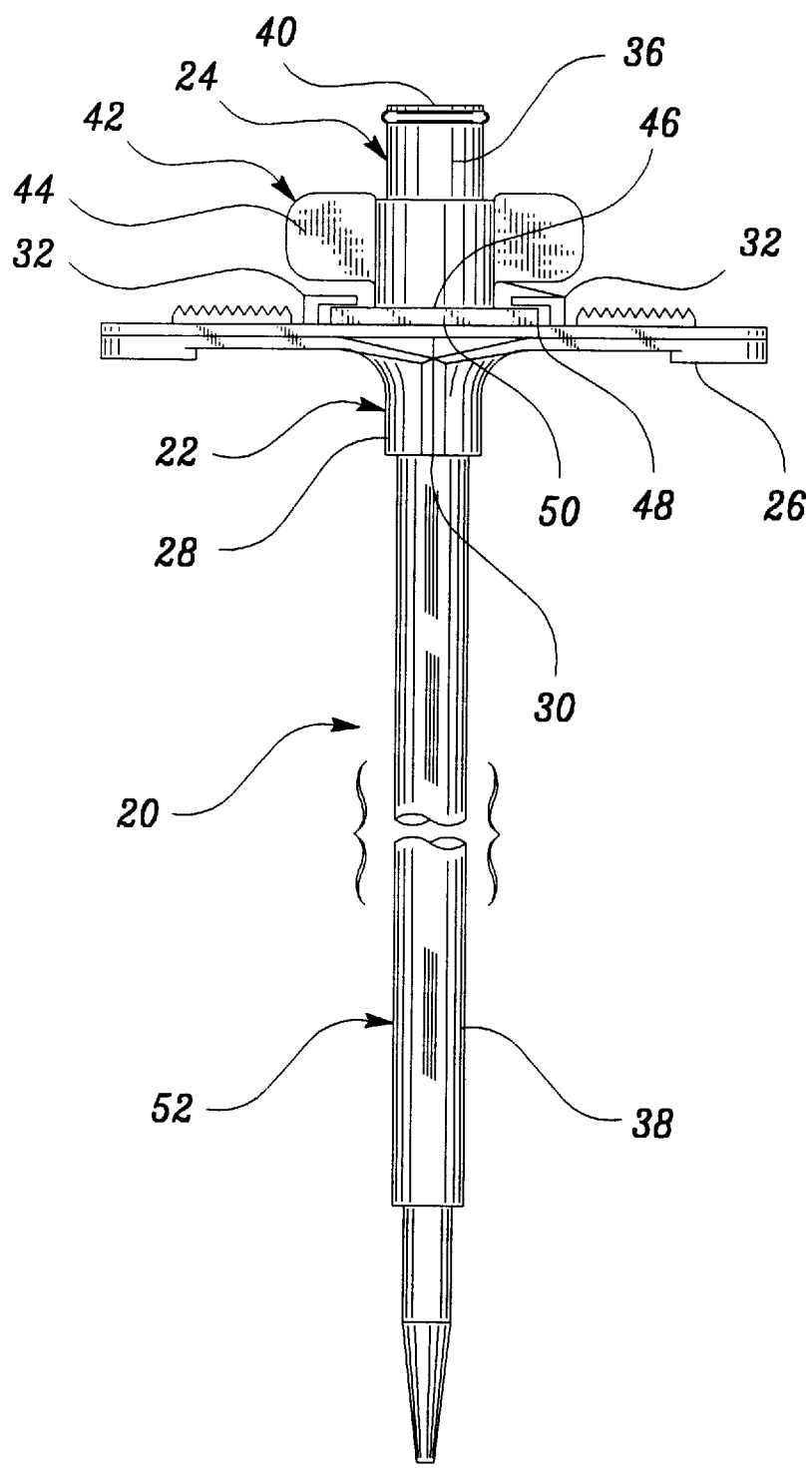
FIG. 13 is an enlarged perspective view showing an alternate form of the dilator member of FIG. 9.

The dilator locking mechanism 42 of the preferred embodiment may also be fixedly connected to or formed as an integral part of the dilator hub 36. This variation of the prior embodiment is particularly useful where the relative rotation of the dilator locking mechanism 42 with the dilator member 24 is not desired or required. For example, the embodiment shown in FIG. 13 may be used with round dilator members 52 where rotational movement of the round dilator member 52 relative to a round sheath member (not shown) is acceptable or in situations where a larger diameter oval shaped sheath member 22 is used with a smaller diameter dilator member (not shown). Additionally, as shown in FIG. 13, a plurality of locking tabs 32 may be used to secure the sheath member 22 and dilator member 24 of the present invention together.

Figure 14:
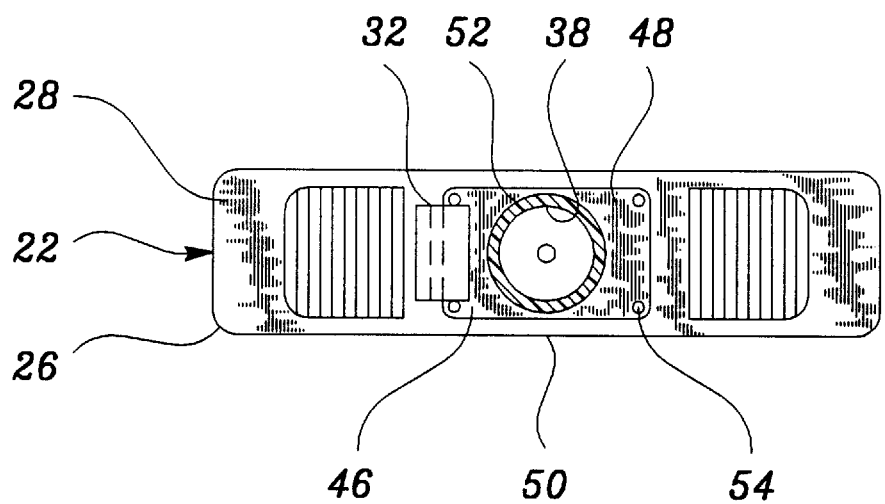
FIG. 14 is a cross-sectional view similar to the view shown in FIG. 11 showing the top portion of an alternate embodiment of the ledge area engaging the sheath member of the catheter introducer of the present invention.
Figure 15:
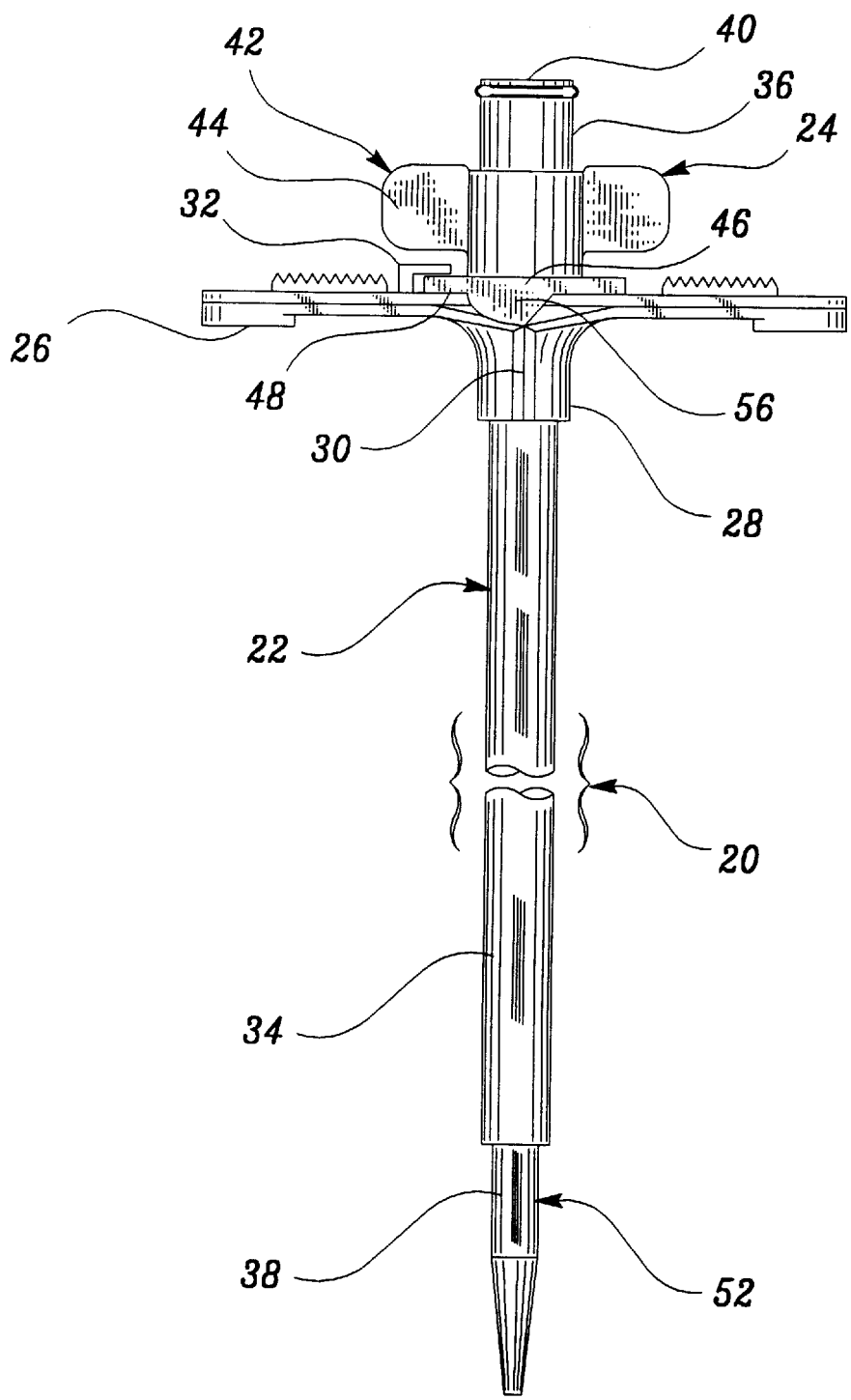
FIG. 15 is a side view of an alternate embodiment of the present invention.

FIGS. 14 and 15 are illustrative of further preferred forms of the present invention. The catheter introducer 20 of these embodiments are generally similar to the embodiments described above and shown in FIGS. 9–13 except that the locking mechanism of the present embodiments are enhanced to provide the user with the ability to feel when the dilator locking mechanism 42 is engaged with the locking tab 32.

FIG. 14 is illustrative of the simplest form of the enhancement wherein a plurality of spaced apart raised teeth or bumps 54 are provided along the distal side of the extension areas 48 on the ledge area 46. The raised bumps 54 are preferably spaced apart a sufficient distance to receive the locking tab 32 therebetween when the locking tab 32 is engaged with the dilator locking mechanism 42. The presence of the raised bumps 54 provide the user with a tactile sensation of when the dilator locking mechanism 42 engages and disengages from the locking tab 32 and also provides an additional area of resistance which must be overcome to disengage the dilator locking mechanism 42 from the locking tab 32 to prevent the inadvertent disengagement thereof.

FIG. 15 is illustrative of a further embodiment having an enhanced locking mechanism. In this embodiment, the dilator locking mechanism 42 is modified to include an enlarged and distally extending bump member 56 which extends distally from the distal side of the ledge area 46. As shown in FIG. 15, the bump member 56 extends from a location on the ledge area 46 which is adjacent to at least one of the flat areas 50 of the ledge area 46 to a location along the slit 30 of sheath hub 28. The bump member 56 is sized and shaped so that when the dilator locking mechanism 42 is engaged with the locking tab 32 on the sheath hub 28, the bump member 56 is positioned between the handle members 26 of the sheath member 22. One or both of the side surfaces of the bump member 56 may be- curved to provide a gradually increasing amount of resistance to the rotation of the dilator locking mechanism 42 from the engaged position to the disengaged position. As the dilator member 42 is rotated from the engaged position to the disengaged position, the bump member 56 may also be sized to initiate the tearing of the pull apart sheath member 22 by causing the handle members 26 to deflect and separate along the slit 30 as the dilator locking mechanism 42 is moved from the engaged to the disengaged position.

FIGS. 16–21 are illustrative of further preferred forms of the present invention. The catheter introducer 20 of these embodiments are generally similar to the embodiments described above and shown in FIGS. 9–13 except that the locking mechanism of the present embodiments are enhanced to provide the user with the ability to rotate the dilator locking mechanism 42 in a single or in both directions to provide secure locking engagement between the modified locking tab, 80 or 82, and the modified dilator locking mechanism, 84 or 86, respectively. These embodiments also allow the user to feel when the modified dilator locking mechanism is engaged with the modified locking tab.

FIG. 16 is illustrative of the simplest form of the modified locking tab 80 and modified dilator locking mechanism 84 wherein the extension area 88 of the ledge area 90 is modified to include a curved lateral surface 92 and a straight surface 94 as shown in FIG. 17. The locking tab 80 of this embodiment is modified to receive the extension area 88 of the dilator locking mechanism 84 in a single direction of rotation such as the counterclockwise direction as shown in FIG. 16. As shown in FIG. 18, the locking tab 80 of this embodiment includes a sidewall 96 which contacts the straight surface 94 of the extension area 88 to prevent additional counterclockwise rotational movement of the dilator locking mechanism 84 once the ledge area 90 is received in the locking tab 80. Although not shown, the locking tab 80 may also include a small ridge member (not shown) opposite the sidewall 96 to contact a portion of the curved lateral surface 92 of the extension area 88 when the straight surface contacts the sidewall 96 to frictionally retain the dilator locking mechanism 84 in the locking tab 80. In this form of the embodiment, the sidewall 96 and ridge member are spaced apart a sufficient distance to receive the extension area 88 therebetween when the locking tab 80 is engaged with the dilator locking mechanism 84. The presence of the sidewall 96 on the locking tab 80 as well as the optional ridge member provides the user with a tactile sensation of when the dilator locking mechanism 84 is engaged with the locking tab 80 and the ridge member also provides an additional area of resistance which must be overcome to disengage the dilator locking mechanism 84 from the locking tab 80 to prevent the inadvertent disengagement thereof during use.

FIGS. 19–21 are illustrative of a further embodiment of the present invention having an enhanced locking mechanism. In this embodiment, the ledge area 90 of the dilator locking mechanism 86 is modified to include a pair of extension areas 88 each having a curved lateral surface 92 and a straight surface 94 thereon. The locking tab 82 of this embodiment is modified to include a central wall member 98 extending from the top surface of the locking tab 82. Therefore, with the embodiment shown in FIGS. 19–21, the dilator locking mechanism 86 may be rotated in either direction with respect to the locking tab 82. Similar to the embodiment described above and shown in FIGS. 16–18, the rotation of the dilator locking mechanism 86 of this embodiment, causes the straight surface 94 of the extension area 88 to contact the central wall member 98 to prevent continued rotational movement of the dilator locking mechanism 86 and to provide the user with a reliable indication that the dilator member 24 is secured to the sheath member 22. This embodiment may also include a pair of ridge members (not shown) spaced apart from the central wall member 98 of the locking tab 82 to provide the user with an additional tactile indicator of the secure engagement between the locking tab 82 and the dilator locking mechanism 86 of the present invention. In addition to the above, the curved lateral surface 92 of the extension area may be tapered to provide a gradually increasing amount of resistance to the rotation of the dilator locking mechanism 86 into the engaged position while not affecting the amount of force necessary to move the dilator locking mechanism from the engaged position to the disengaged position.

Figures 22, 23:
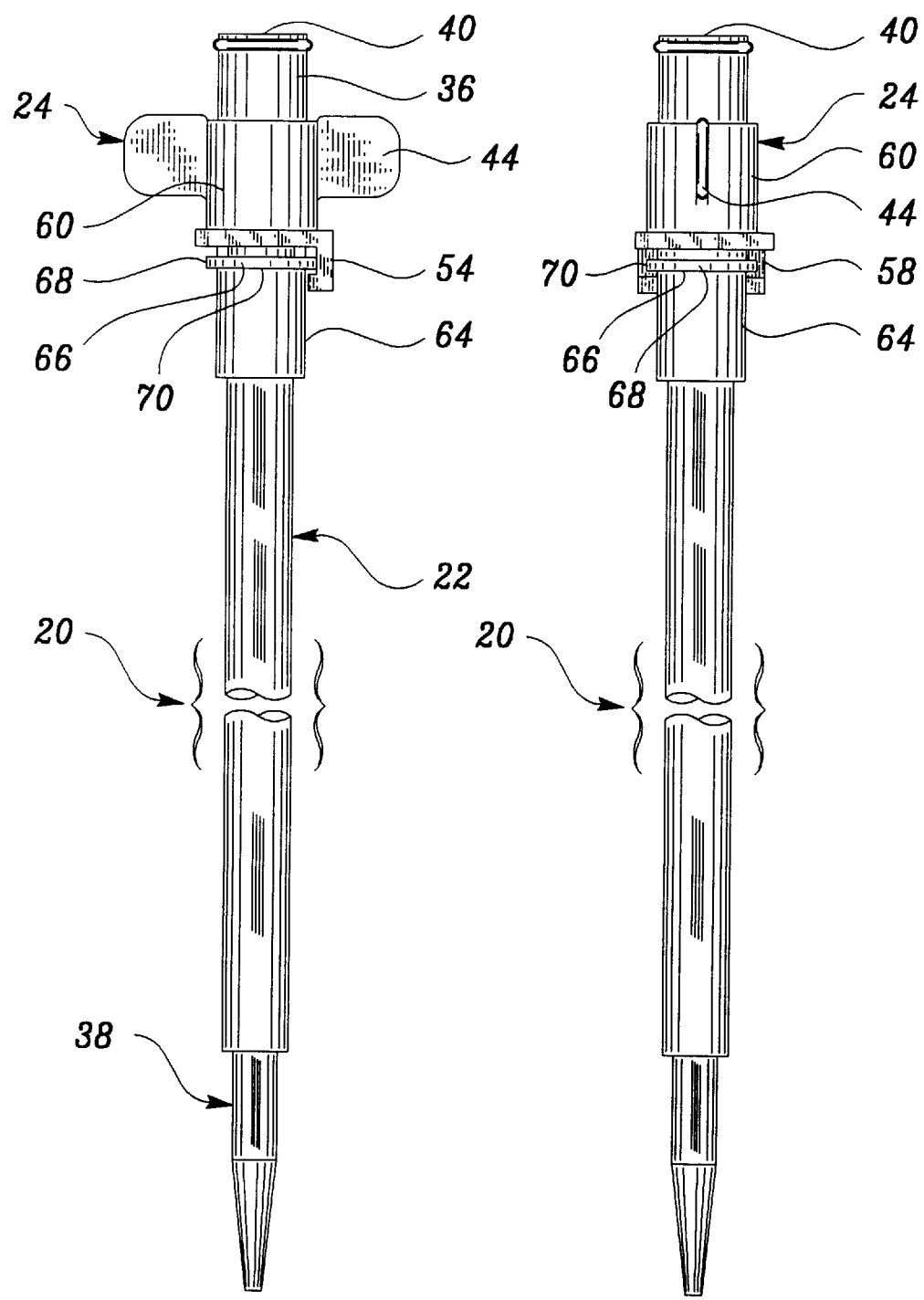
FIG. 22 is a side view of an alternate embodiment of the present invention showing the dilator locking mechanism in engagement with the sheath hub.
FIG. 23 is a side view of the embodiment of FIG. 16 showing the dilator locking mechanism disengaged with the sheath hub from the left side of FIG. 16.

As shown in FIGS. 22 and 23, the catheter introducer 20 of the present invention may also include a locking tab 58 which extends distally from the modified dilator locking mechanism 60 to cooperate with the ledge area 66 on the sheath hub 64. As with the embodiments described above, the modified dilator locking mechanism 60 may be rotatable or fixed with respect to the dilator hub 36. The distal end portion of the sheath hub 64 of this embodiment is preferably round and is provided with a ledge area 66 having one or more extension areas 68 and one or more flat areas 70 similar to those described above with respect to the ledge area 46 on the dilator locking mechanism 42. The ledge area 66 preferably extends around the entire opening of the sheath hub 64 which is shown in this embodiment as a non-tearable sheath member. In the event that it is desired to use a tearable sheath member of the type shown in FIG. 8 in combination with the embodiment shown in FIGS. 22 and 23, it is anticipated that the sheath hub 64 may be modified so that the ledge area 66 is formed by a plurality of recesses or grooves formed in the handle members (not shown) rather than as a generally circumferential member on the distal end portion of the sheath hub 64. Alternately, the ledge area 66 may be formed on a proximally extending surface located proximally of the handle members on the sheath hub 64.

The foregoing is intended to be illustrative of the currently preferred embodiments of the present invention. While it is believed that a person skilled in the art may foresee various modifications of the presently preferred embodiments from the teachings set forth above, the scope of the present invention should be interpreted in accordance with the following claims.

What is claimed is:

1. A catheter introducer comprising:

a sheath section having distal and proximal end portions;

a generally cylindrical sheath hub formed on said proximal end Portion of said sheath section, said sheath hub including one or more handle members extending laterally therefrom, an outer circumference and a longitudinal passageway extending therethrough;

a generally elongate and tubular sheath member formed on said distal end portion of said sheath section and including a longitudinal passageway extending therethrough and said passageway extending in flow communication with said passageway of said sheath hub;

a dilator section having distal and proximal end portions thereon and said dilator section being operatively associated with said sheath section in use;

a generally cylindrical dilator hub formed on said proximal end portion of said dilator section;

a dilator locking mechanism operatively associated with said dilator section, said dilator locking mechanism including one or more enlarged flange members extending laterally from a portion thereof and said flange members being sized to be rotatable manipulated with respect to said sheath hub;

a locking mechanism operatively associated with said sheath hub and said dilator locking mechanism wherein said locking mechanism is movable between a first position wherein said flange members of said dilator locking mechanism are laterally aligned with said one or more handle members of said sheath hub and said dilator section is coupled to said sheath section and a second position wherein said dilator section is separable from said sheath section; and wherein said one or more flange members are rotatable with respect to said dilator section.

2. The catheter introducer of claim 1 wherein said locking mechanism includes a tab member extending from one of said dilator locking mechanism or said sheath section.

3. The catheter introducer of claim 2 wherein said locking mechanism includes a ledge area extending laterally from the other of said dilator locking mechanism or said sheath section.

4. The catheter introducer of claim 2 wherein said locking mechanism includes a ledge area extending laterally from the other of said dilator locking mechanism or said sheath section and said ledge area includes at least one flat area and at least one extension area thereon.

5. The catheter introducer of claim 2 wherein said locking mechanism includes one or more bumps thereon to provide a tactile indication of the movement of said locking mechanism between said first and second positions.

6. The catheter introducer of claim 1 wherein said outer circumference of said dilator locking mechanism includes a ledge area thereon which is engaged by a tab member on said sheath hub in said first position of said locking mechanism.

7. The catheter introducer of claim 1 wherein said sheath hub includes one or more handle members extending laterally therefrom.

8. The catheter introducer of claim 1 wherein said sheath hub includes a slit therein.

9. The catheter introducer of claim 1 wherein a guide wire receiving channel extends through the entire lengthwise dimension of said dilator section.

10. The method of claim 1 wherein the initial application of a rotational force to the flange member causes a locking tab which is prevented from longitudinal movement along the dilator member to engage a laterally extending ledge area on the sheath hub.

11. A catheter introducer comprising:

a sheath section having distal and proximal end portions;

a generally cylindrical sheath hub formed on said proximal end portion of said sheath section, said sheath hub including an outer circumference and a longitudinal passageway extending therethrough;

a generally elongate and tubular sheath member formed on said distal end portion of said sheath section and including a longitudinal passageway extending therethrough and said passageway extending in flow communication with said passageway of said sheath hub;

a dilator section having distal and proximal end portions thereon and said dilator section being operatively associated with said sheath section in use;

a generally cylindrical dilator hub formed on said proximal end portion of said dilator section;

a dilator locking mechanism operatively associated with said dilator section, said dilator locking mechanism including one or more enlarged flange members extending laterally from a portion thereof and said flange members being sized to be rotatably manipulated with respect to said sheath hub and said dilator hub; and a locking mechanism operatively associated with said sheath hub and said dilator locking mechanism wherein said locking mechanism is movable between a first position wherein said dilator section is coupled to said sheath section and a second position wherein said dilator section is separable from said sheath section.

12. The catheter introducer of claim 11 wherein said locking mechanism includes a tab member extending from one of said dilator locking mechanism or said sheath section.

13. The catheter introducer of claim 11 wherein said looking mechanism includes a ledge area extending laterally from the other of said dilator locking mechanism or said sheath section.

14. The catheter introducer of claim 12 wherein said locking mechanism includes a ledge area extending laterally from the other of said dilator locking mechanism or said sheath section and said ledge area includes at least one flat area and at least one extension area thereon.

15. A method of using a catheter introducer, including the steps of:

inserting a dilator member having a dilator hub and dilator portion thereon into a sheath member having a sheath hub and a sheath portion thereon such that an enlarged flange member operatively associated with the dilator hub is misaligned with a laterally extending handle member on the sheath member;

rotating the flange member into alignment with the handle member on the sheath member so that a locking mechanism associated with the dilator member lockingly engages a portion of the sheath member to prevent longitudinal movement therebetween;

inserting a portion of the catheter introducer into the body of a patient by rotational and longitudinal movement of the catheter introducer; and applying a rotational force to the flange member with respect to the sheath hub and dilator hub to release the dilator member from the sheath hub to allow longitudinal movement between the dilator member and the sheath member.

16. The method of claim 15 wherein the application of a rotational force to the flange member with respect to the sheath member releases a locking mechanism which secures the dilator member to the sheath member.

17. The method of claim 15 wherein the initial application of a rotational force to the flange member causes a locking tab which is prevented from longitudinal movement along the dilator member to engage a laterally extending ledge area on the sheath hub.

18. The method of claim 15 wherein the further application of a rotational force to the flange member causes the locking tab to disengage from the ledge area of the sheath hub to allow longitudinal movement between the dilator member and the sheath member.

* * * * *